US005922163A

United States Patent [19]

Helynranta et al.

[11] Patent Number: 5,922,163

[45] Date of Patent: Jul. 13, 1999

[54] METHOD FOR MANUFACTURING AN ABSORBENT COMPOSITE IN A SANITARY PRODUCT, AND AN ABSORBENT COMPOSITE MANUFACTURED WITH THE METHOD

[75] Inventors: Pekka Helynranta, Egå; Stefan Favre, Risskov, both of Denmark; Helmer Gustafsson, Valkeakoski, Finland

[73] Assignee: Yhtyneet Paperitehtaat Oy, Valkeakoski, Finland

[21] Appl. No.: 08/608,320

[22] Filed: Feb. 28, 1996

[30] Foreign Application Priority Data

Mar. 1, 1995 [FI] Finland .................................... 950922

[51] Int. Cl.$^{6}$ .............................. D04H 3/16; A61F 13/15

[52] U.S. Cl. ............................................ 156/296; 604/367

[58] Field of Search .................................... 156/227, 296, 156/62.2, 62.4, 62.6, 62.8, 279; 604/384, 367, 368

[56] References Cited

U.S. PATENT DOCUMENTS 4,079,739 3/1978 Whitehead .
4,551,378 11/1985 Carey, Jr. .
4,732,809 3/1988 Harris, Jr. et al. .
5,549,775 8/1996 Odorzynski ............................ 156/227

FOREIGN PATENT DOCUMENTS 0 269 380 6/1988 European Pat. Off. .
0 306 262 3/1989 European Pat. Off. .
0 441 064 8/1991 European Pat. Off. .
54 995 1/1979 Finland .
43 05 271 8/1994 Germany .
185 228 10/1963 Sweden .
334 335 4/1971 Sweden .
WO 93/06804 4/1993 WIPO .
WO 94/10957 5/1994 WIPO .

*Primary Examiner*—David J. Isabella
*Assistant Examiner*—John M. Black
*Attorney, Agent, or Firm*—Young & Thompson

[57] ABSTRACT

A method for manufacturing an absorbent composite in a sanitary product wherein at least one liquid absorbing layer (14) is formed by the dry forming technique. The absorbing layer includes natural fibers, such as wood fibres, or natural fibers and plastic fibers mixed with one another, and super-absorbent material (15), and is bound by heat. At least one material layer (13) is dry formed on the absorbing layer (14), before the absorbing layer is bound by heat, from fibers crimping in connection with the binding taking place by heat.

10 Claims, 1 Drawing Sheet

9
13
14
15
16

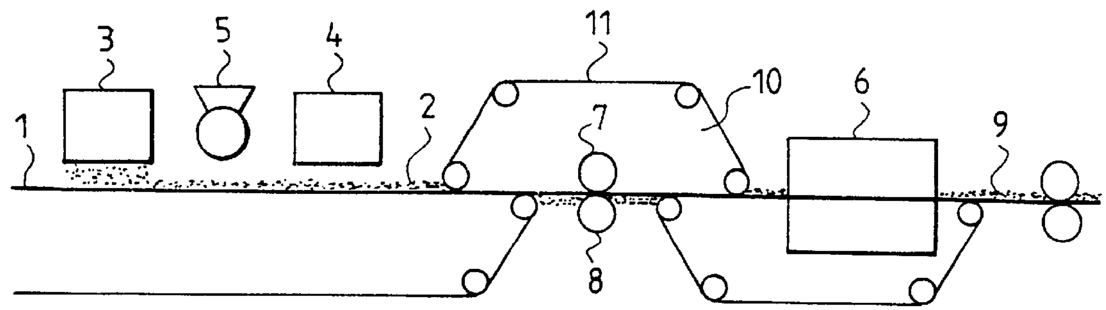
FIG. 1
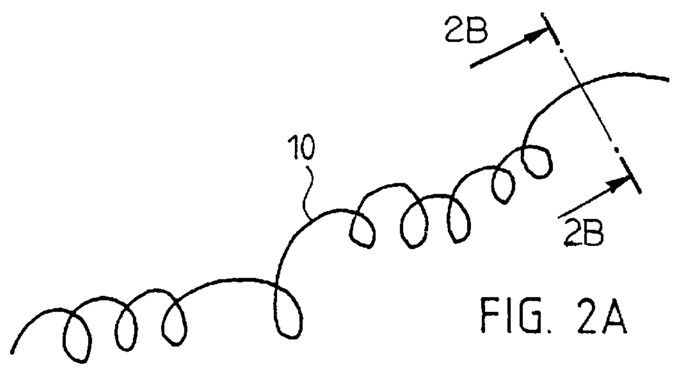
FIG. 2A
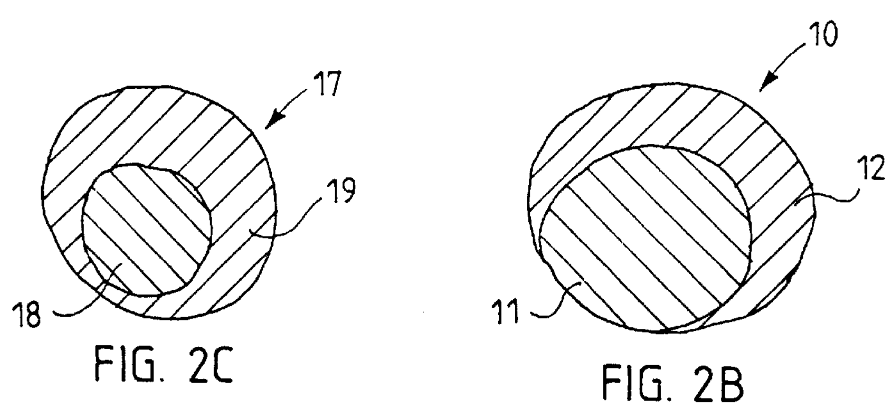
FIG. 2C
FIG. 2B
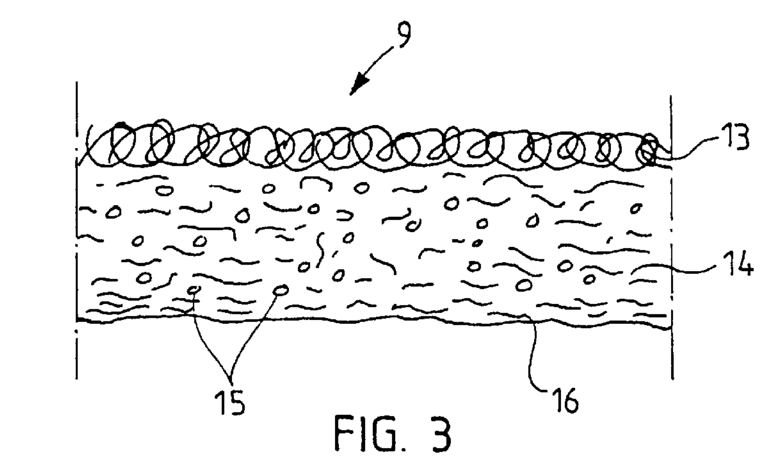
FIG. 3

METHOD FOR MANUFACTURING AN ABSORBENT COMPOSITE IN A SANITARY PRODUCT, AND AN ABSORBENT COMPOSITE MANUFACTURED WITH THE METHOD

FILED OF THE INVENTION

The present invention relates to a method for manufacturing an absorbent composite in a sanitary product, wherein at least one liquid absorbing layer is formed by means of the dry forming technique, which absorbing layer comprises natural fibres, such as wood fibres, or natural fibres and plastic fibres mixed with one another, and superabsorbent material, and which is bound by means of heat. The present invention also relates to an absorbent composite in a sanitary product, manufactured with the method, which absorbent composite comprises at least one dry-formed absorbing layer, which comprises natural fibres, such as wood fibres, or natural fibres and plastic fibres mixed with one another, and superabsorbent material, and which is bound by means of heat, and at least one liquid dispersive material layer on the absorbing layer.

BACKGROUND OF THE INVENTION

In manufacturing dry formed sanitary products, an absorbent composite is formed by means of the dry forming technique from natural fibres, to which is added a binding material or binding fibres, which bind the formed material web into a porous material layer by the action of heat. The absorbent composite may consist of several superimposed layers according to desired thickness. Superabsorbent material is often added locally to the absorbent composite to improve absorption capacity. Such absorbent composites are disclosed for instance in WO publications 93/06804 and 94/10957.

Material composites manufactured in this manner are used for manufacturing different diapers, incontinence products and sanitary towels. Recently, the size of such products has been reduced in order that they would be as inconspicuous as possible, and as, on the other hand, the object has been to achieve as good an absorption capacity as possible, attempts have been made to solve the problem by increasing the amount of the superabsorbent material. Such products have typically consisted of two material layers, a liquid wicking layer and a liquid absorbing layer. Both layers usually consist of natural fibres or a mixture of natural fibres and binding fibres. In addition, superabsorbent material is usually added to a layer which faces away from the user. A great disadvantage of such products is the fact that the layer which faces the user remains damp, as a result of which a relatively thick liquid-repellent cover stock must be added to the final product in order that the product would feel dry against the skin of the user.

Another disadvantage of such products is the fact that liquid is absorbed rather slowly through the structure due to the porous fibre-like structure, as a result of which only a part of the absorption capacity of a sanitary product is utilized effectively in practice.

SUMMARY OF THE INVENTION

The object of the present invention is to provide a method for manufacturing such an absorbent composite in a sanitary product which has very good surface dryness characteristics, a good liquid wicking and absorbing capacity, and a small size. To achieve this, the method of the invention is characterized in that at least one material layer is dry formed on the absorbing layer, before the absorbing layer is bound by means of heat, from fibres crimping in connection with the binding taking place by means of heat. Preferably, the lower surface of the absorbing layer, before it is bound with heat, is hot calendered with a roll to achieve a desired liquid wicking capacity.

The preferred absorbent composite of the invention is thus produced essentially in such a manner that the absorbent composite comprises material layers for wicking liquid and for absorbing liquid and an extremely porous and soft cover stock, which quickly lets liquids pass through to lower layers by retaining its dryness and separating the damp layers from the user of the product.

The absorbent composite of the invention is characterized in that the liquid dispersive material layer is dry formed from fibres crimping by the action of heat, and that the absorbent composite is formed essentially as one layer by the dry forming technique, and the fibres of the absorbing layer and the fibres of the liquid dispersive material layer are bound and the fibres of the liquid dispersive layer are crimped during one heating. The final result is thus an absorbent composite which is extremely absorbent and small in size and which has no particle or other concentrations which would deteriorate mechanical durability.

The other preferred embodiments of the method of the invention are characterized by what is disclosed in the claims presented below. The other embodiments of the absorbent composite in a sanitary product according to the invention are also characterized by what is disclosed in the claims presented below.

BRIEF DESCRIPTION OF THE FIGURES

The method of the invention and the absorbent composite in a sanitary product, manufactured by means thereof, will be described in more detail in the following with reference to the accompanying drawing, in which FIG. 1 shows a production line for the absorbent composite in a sanitary product according to the invention, FIGS. 2*a*–2*c* show eccentric bicomponent fibres, and FIG. 3 shows a cross section of the absorbent composite in a sanitary product according to the invention.

DETAILED DESCRIPTION OF THE PREFERRED EMBODIMENTS

FIG. 1 shows a dry forming line, in which a material web 2 is formed on a wire 1 in two stages by means of two formers 3 and 4. The liquid absorbing layer is formed by the former 3 from natural fibres, such as wood fibres, or from a mixture of natural fibres and plastic fibres, and superabsorbent material, and the cover stock is formed by the former 4 from fibres crimping by the action of heat. A mixture of air and fibre is blown into the formers, which extend transversely across the wire over its entire width, this mixture being mixed and screened to form an even material layer onto the wire 1 moving below in accordance with prior art. It is possible to dispose as many formers as the desired thickness of the material web 2 requires, whereby the thickness of the material web is gradually increased by means of formers arranged successively on the same production line until the desired thickness is achieved. The proportion of wood fibres to plastic fibres in material web layers produced by different formers may thus vary.

The wood fibres are preferably relatively long-fibred mechanical or chemical pulp, and the plastic fibres of the liquid absorbing layer may be any suitable heat bindable fibres, for instance bicomponent fibres, the core of which is polypropylene and the coat of which is polyethene.

Superabsorbent particles or superabsorbent fibres are added to the material web 2 either by means of a separate sprinkling device 5 or by adding them to the fibre material of the former 3. Suitable superabsorbent materials are for instance activated carbon, activated clay, silica gels, CMC-based superabsorbents and crosslinked polyacrylates. The superabsorbent may also be in a liquid form, spraying nozzles being thus used instead of a sprinkling device for spraying for instance acrylic acid monomer in aqueous dispersion onto the material web. The monomers are cross-linked by means of heat and a suitable radical, the super-absorbent thus binding the fibres together for its part. The amount of plastic fibres can thus be decreased in this layer, or they can be omitted altogether as unnecessary.

The percentage limits of different particles in the absorbing layer may be for instance as follows: wood fibre (chemical pulp fibre) 10–90%, plastic fibre 0–70% and superabsorbent particles 0–90% The grammage of the cover stock may be for instance 15–100 $g/m^2$ and that of the entire absorbent composite for instance 80–1000 $g/m^2$.

After the forming stage, the lower surface of the absorbing layer is calendered with a hot roll 8 to achieve a desired liquid wicking capacity. This calendering of the lower surface of the absorbing layer takes place when the material web is being sucked against the wire 11 which moves round a suction box 10. Patterning which improves the spreading of liquid to desired areas of the product can be produced either by means of a smooth calender roll and a patterned wire or by means of an embossing calender roll and a smooth wire. It has been shown that liquid spreads faster, up to a certain limit, in a denser fibre layer as compared with a more porous fibre layer. This is based on the fact that more densely packed fibres have a greater liquid spreading capacity than fibres which are farther apart from one another. By utilizing this characteristic and providing the liquid with "passages" along which it is capable of travelling faster to all parts of the product, the absorption capacity of the product is utilized in an optimum manner. After the calendering, the material web is bound with heat in a dryer 6. Both the fibres of the absorbing layer and those of the cover stock as well as the superabsorbent material included in the absorbing layer are thus bound together at a time, be the superabsorbent material either fibre-like, particle-like or liquid.

FIG. 2*a* shows an eccentric bicomponent fibre 10 crimped by means of heat. FIG. 2*b* shows a cross section of the fibre appearing in FIG. 2*a* as taken along the line 2B—2B shown in FIG. 2*a*. It appears from the cross section shown in FIG. 2*b* that the core 11 of the eccentric fibre 10 is located eccentrically with respect to a coat 12 in such a manner that the core extends to the outer rim. FIG. 2*c* shows a cross section of a centrically eccentric bicomponent fibre 17, the core 18 of which is also located eccentrically in a coat 19, but in such a manner that it does not extend to the outer rim. The cores 11 and 18 of the fibres 10 and 17, respectively, are preferably polypropylene, and the coats 12 and 19 are polyethene. In binding the eccentric bicomponent fibres according to FIGS. 2*a–c* by means of heat, they are considerably curled or crimped, forming a great number of binding points, whereby the result is an extremely porous and elastic fibre layer. The thickness of eccentric bicomponent fibres used in the cover stock is preferably 0.8–12 dTex and the length 3–12 mm.

FIG. 3 shows a cross section of the absorbent composite in a sanitary product according to the invention, the cross section showing a cover stock 13, which consists exclusively of eccentric bicomponent fibres, and an absorbing layer 14, which consists of wood fibres or a mixture of wood fibres and plastic fibres, and of superabsorbent material 15. In FIG. 3, the superabsorbent material is shown as particle-like. If a fibre-like or liquid superabsorbent material were used instead of the particles, this material would not be appreciably distinguished from the rest of the structure of the absorbing layer, wherefore these alternatives are not separately shown.

It appears from the cross section according to FIG. 3 that the entire absorbent composite 9 is essentially one seamless layer, one surface of which is a cover stock consisting of eccentric bicomponent fibres and the other surface of which is an absorbing layer containing superabsorbent material. The thickness of the layers can be varied and adjusted at the forming stage, the only essential aspect being that the layers are formed on the same line and bound together during one stage. The final product, formed from the fibre layer, is cut to a suitable size and its lower surface is possibly covered with a liquid impermeable plastic layer. Other possibly required finishing procedures depend on the use of the final product.

The method of the invention for manufacturing an absorbent composite in a sanitary product as well as the absorbent composite in a sanitary product manufactured by means thereof have been described above by means of only some exemplifying embodiments, and it will be apparent to one skilled in the art that the different embodiments of the invention are not restricted to the examples presented above but that they may vary within the scope of the claims presented below.

We claim:

1. A method of manufacturing an absorbent composite in a sanitary product, which comprises the steps of:

forming at least one liquid absorbing layer by a dry forming technique, said absorbing layer including natural fibres and plastic fibres mixed with one another, and super-absorbent material;

dry forming at least one material layer on the absorbing layer, said material layer including fibres crimping in connection with heat binding; and heat binding the absorbent composite.

2. The method according to claim 1, wherein a lower surface of the absorbing layer, before heat binding, is hot calendered with a roll to achieve a desired liquid wicking capacity.

3. The method according to claim 2, wherein the hot calendering of the lower surface of the absorbing layer is performed with a patterned roll to produce patterning which improves spreading of liquid at a level of the fibre layer.

4. The method according to claim 2, wherein the hot calendering of the lower surface of the absorbing layer is performed with a smooth roll, whereafter a final calendering of the fibre layer is performed with a patterned roll to produce patterning which improves spreading of liquid at a level of the fibre layer.

5. The method according to claim 1, wherein the superabsorbent material is added in particle or fibrous form by a separate sprinkling device.

6. The method according to claim 1, wherein the superabsorbent material is added in particle or fibrous form to a flow of fibres forming the absorbing layer at a forming stage of the layer.

7. The method according to claim 1, wherein the superabsorbent material is added in particle or fibrous form both by a separate sprinkling device and to a flow of fibres forming the absorbing layer at a forming stage of the layer.

8. The method according to claim 1, wherein the superabsorbent material is added in liquid form to the absorbing layer immediately after the layer has been dry formed.

9. The method according to claim 1, wherein the material layer consisting of crimping fibres is dry formed from eccentric bicomponent fibres having a core which extends to an outer rim.

10. The method according to claim 1, wherein the material layer consisting of crimping fibres is dry formed from eccentric bicomponent fibres having a core which does not extend to an outer rim.

* * * * *